US010109457B2

(12) United States Patent
Lopour et al.

(10) Patent No.: US 10,109,457 B2
(45) Date of Patent: Oct. 23, 2018

(54) METHOD OF SPECIMEN PROCESSING IN AN APPARATUS WITH TWO OR MORE PARTICLE BEAMS AND APPARATUS FOR THIS PROCESSING

(71) Applicant: TESCAN ORSAY HOLDING, A.S., Brno (CZ)

(72) Inventors: Filip Lopour, Brno (CZ); Tomas Hrncir, Ricmanice (CZ)

(73) Assignee: Tescan Orsay Holding, A.S., Brno (CZ)

( * ) Notice: Subject to any disclaimer, the term of this patent is extended or adjusted under 35 U.S.C. 154(b) by 79 days.

(21) Appl. No.: 14/904,409

(22) PCT Filed: Jul. 9, 2014

(86) PCT No.: PCT/CZ2014/000078
§ 371 (c)(1),
(2) Date: Jan. 11, 2016

(87) PCT Pub. No.: WO2015/003671
PCT Pub. Date: Jan. 15, 2015

(65) Prior Publication Data
US 2016/0148783 A1 May 26, 2016

(30) Foreign Application Priority Data

Jul. 11, 2013 (CZ) .................................... 2013-547

(51) Int. Cl.
*G01N 1/28* (2006.01)
*H01J 37/30* (2006.01)
*G01N 1/32* (2006.01)

(52) U.S. Cl.
CPC ............ *H01J 37/3005* (2013.01); *G01N 1/32* (2013.01); *H01J 2237/20207* (2013.01);
(Continued)

(58) Field of Classification Search
CPC ......... H01J 2237/31745; H01J 37/3005; H01J 2237/31749; H01J 2237/304; H01J 2237/20207; G01N 1/28; G01N 1/32
See application file for complete search history.

(56) References Cited

U.S. PATENT DOCUMENTS

| 5,892,225 A * | 4/1999 | Okihara | G01R 31/307 250/307 |
|---|---|---|---|
| 5,986,264 A | 11/1999 | Gruenewald | |

(Continued)

FOREIGN PATENT DOCUMENTS

JP 2012113865 A 6/2012

OTHER PUBLICATIONS

Kwakman L et al: "Characterization and Failure Analysis of 30 Integrated System using a novel plasma-FIB system", AIP Conference Proceedings American Institute of Physics USA, vol. 1395, 2011, pp. 269-273, XP55167790, ISSN: 0094-243X, DOI: 10.1063/1.3657902.

(Continued)

*Primary Examiner* — Brooke Purinton
(74) *Attorney, Agent, or Firm* — Thedford I. Hitaffer; Hitaffer & Hitaffer, PLLC

(57) ABSTRACT

A method and apparatus for processing a specimen with two or more particle beams, wherein the specimen has a milled side that is processed by a first particle beam and observed by a second particle beam. The specimen is milled during a first milling operation by the first particle beam with the specimen in a first position. Thereafter, the specimen tilts in a second position around an axis of tilt of the specimen. Thereafter, the specimen is milled during a second milling operation. Milling can be performed during continuous tilting of the specimen around the axis of tilt. The axis of tilt of the specimen intersects the milled side. In all the aforementioned positions of the specimen, the second particle (Continued)

beam impinges on the milled side, which enables monitoring of the milling in real time.

20 Claims, 6 Drawing Sheets

(52) U.S. Cl.
CPC .............. *H01J 2237/304* (2013.01); *H01J 2237/31745* (2013.01); *H01J 2237/31749* (2013.01)

(56) References Cited

U.S. PATENT DOCUMENTS

| | | | |
|---|---|---|---|
| 7,700,931 B2* | 4/2010 | Shichi | H01J 37/20 250/306 |
| 2008/0258056 A1* | 10/2008 | Zaykova-Feldman | G01N 23/04 250/307 |
| 2008/0315088 A1 | 12/2008 | Takahashi | |
| 2010/0116977 A1* | 5/2010 | Young | G01N 1/286 250/252.1 |
| 2013/0240353 A1 | 9/2013 | Watanabe | |
| 2014/0061032 A1* | 3/2014 | Miller | G01N 1/32 204/192.33 |
| 2015/0243478 A1* | 8/2015 | Lee | H01J 37/3056 204/192.11 |
| 2015/0276567 A1* | 10/2015 | Schmidt | G01N 1/32 250/307 |
| 2017/0140897 A1* | 5/2017 | Phaneuf | H01J 37/3056 |

OTHER PUBLICATIONS

European Patent Office, International Searching Authority, Written Opinion, dated Feb. 27, 2015, in International Application No. PCT/CZ2014/000078, filing date Jul. 7, 2014.

European Patent Office, International Searching Authority, International Search Report, dated Feb. 27, 2015, in International Application No. PCT/CZ2014/000078, filing date Jul. 7, 2014.

Giannuzzi LA and Stevie FA (edts): "Introduction to Focused Ion Beams—Instrumentation, Theory, Techniques and Practice" (2005), Springer Science + Business Media Inc., XP055168900, ISBN: 0-387-23116-1, relevant pp. 107-142, 247-268.

* cited by examiner

METHOD OF SPECIMEN PROCESSING IN AN APPARATUS WITH TWO OR MORE PARTICLE BEAMS AND APPARATUS FOR THIS PROCESSING

This application, filed under 35 USC 371, is a United States National Stage Application of International Application No. PCT/CZ2014/000078, filed Jul. 9, 2014, which claims priority to CZ Application No. PV 2013-547, filed on Jul. 11, 2013, the disclosures of which are incorporated herein by reference.

FIELD OF TECHNOLOGY

The presented invention deals with the method and apparatus for processing a specimen in an apparatus with two or more particle beams which enables manipulation with the sample so that the specimen surface can be milled with the first particle beam impinging on the surface at an angle between 0° and 30° gradually from various directions in order to eliminate the curtaining effect, while the milled surface is observed by the second particle beam at the same time or at selected intervals. It is not necessary to change the position of the specimen during the observation with respect to the position during the milling process.

BACKGROUND

In the process of the focused ion beam specimen processing, hereinafter also referred to as FIB, it is necessary to achieve as planar surface of the milled area as possible. One of the applications where this planar surface is desirable is represented for example by TSV structure cuts, where TSV stands for through-silicon vias and comprises silicone plates with e.g. embedded copper structures. Due to various material and milling ratios, the FIB processing leads to the so called curtaining effect, when grooves appear in the line of the beam incidence. It means that a structure with grooves appears on the milled surface, the grooves being formed in the direction of the beam incidence, which is highly undesirable for applications which require plane surface and/or constant thickness for further examination.

One method which is successfully used to reduce the above mentioned effect, is based on polishing the specimen surface by repeated re-scanning by the FIB beam, the axes of which form an angle with the original ones in the plane of the specimen surface, usually an angle in the interval of 5-25°. Grooves originated from the first scanning are practically erased with the second re-scanning using a different angle which results in a smooth, nearly plane surface. Re-scanning by FIB using two different angles in the plane of the milled side is usually achieved by turning the specimen around the axis perpendicular to the milled side by these two angles while milling by FIB is done in each of the positions. This process of re-polishing by tilting the specimen and milling in tilted positions is described, for example, in the article called Characterization and Failure Analysis of 3D Integrated Systems Using a Novel Plasma-FIB System written by Laurens Kwakman, German Franz, Maaike Margrete Visser Taklo, Armin Klumpp, and Peter Ramm, which was published in the AIP Conf. Proc. 1395 Collection FRONTIERS OF CHARACTERIZATION AND METROLOGY FOR NANOELECTRONICS, pages 269-273.

In most applications, it is necessary to monitor the milled surface during the milling process (end-point detection). For example, with TSV structures, the milling process must be stopped in the middle of TSV structure which is to be further examined, in other cases, milling the specimen to exactly defined thickness is necessary, etc.

All the known applications pose a disadvantage in the sense that they do not enable this simultaneous monitoring by observing the milled surface directly during milling or at least by individual stages of milling without further manipulation with the specimen. The problem is, that the position of the milled surface used for milling by FIB does not enable observing this milled surface using the FIB beam. During the milling process, the FIB beam is tangential or nearly tangential to the surface which is to be imaged.

One of the options is to tilt, after a period of milling, the specimen by several tens of degrees into the FIB observation position and backwards, but this causes a delay, brings errors due to the repeatability of the manipulator and it does not allow for the observation of the milling process in real time. Therefore, it is impossible to control the milling process adequately and timely correction of the milling parameters or its timely halt is not possible either, which may even lead to the destruction of the structure that was to be originally examined.

Using the FIB beam for milling and imaging is described for example in the US patent application 2012/0091360 A1. This application also deals with the problems in imaging when using ion beam with plasma source. A beam capable of milling with sufficient efficiency would mill the specimen too intensively during the imaging too, which is absolutely undesirable. That is why the application US 2012/0091360 A1 proposes to make radical changes in the ion beam parameters, such as different excitation of the ion optics elements in the beam path, various diaphragms limiting the beam, etc. as well as changes related to ion sources, between milling and imaging. Xe ions are proposed for milling, while H ions are preferred for imaging, there are also variations in gas pressures and RF sources frequencies and performance. These changes of parameters are, of course, complicated from the point of view of technology and they are expensive. The apparatus described in the application US 2012/0091360 A1 does not enable milling and observing the specimen at the same time.

There are solutions which enable monitoring the process of milling or its depth; however, these solutions cannot be combined with the specimen surface polishing. These solutions are realized in apparatuses with two particle beams. In these apparatuses usually one beam, the FIB beam, serves for the purposes of milling the specimen surface and the other beam, usually the electron one from scanning electron microscope, hereinafter referred to as SEM, is used to image the milled surface. Substantial disadvantage of these solutions is the fact that especially in the case when the specimen must be tilted in order to get polished with FIB, observing and checking with the second beam is impossible, at least in one of the tilted positions. Common configuration does not allow for the second beam to "see" the milled surface, i.e. to form a reasonably big angle with this surface in both tilted positions.

In the so far known solutions, the specimen is placed in the specimen holder, which is attached to the manipulator, and at the same time the manipulator enables the specimen to move and/or to turn. Manipulators commonly allow for a movement along three axes X, Y, and Z which are perpendicular to one another with a possibility of supplementary rotations or tilts. Rotation is the most frequent, usually with no angle limits, i.e. of up to 360°, around perpendicular axis, supplemented possibly by a tilt, limited to an acute angle, e.g. max. 45° around one of the horizontal axes X or Y. In the case of using the tilt of the specimen, the originally vertical rotation axis usually tilts by the same angle.

FIB and SEM axes are usually intersecting and both beams point to the area where the milled specimen is. Apart from this, the mutual position of the FIB and SEM is also limited by physical dimensions of these apparatuses.

Tilt of the specimen using the manipulator serves for the specimen to be set in a position suitable for the required application. For the observing in SEM itself, it is the non-tilted position with the surface of the specimen holder perpendicular to the SEM axis. For processing by FIB, the specimen is usually tilted so that the FIB beam in the middle position of scanning impinges on the processed surface either approximately perpendicularly or approximately tangentially. The middle position of scanning is a position where scanning coils or electrodes do not deflect the beam from its original direction, which is usually also the middle position between the highest deviations to both sides in the directions the scanning is performed in. For the applications of the TSV structure studies type, and also for numerous other ones, approximate tangential milling is advantageous.

In one of the known embodiments, the FIB and SEM axes form an angle of about 50° and the surface of the specimen holder is perpendicular to the SEM axis in its initial position. In this particular case, in order to mill the specimen side perpendicular to the specimen holder approximately tangentially by the FIB beam, the specimen holder must be tilted of about 50° compared to its initial position. In this position, the SEM beam forms in its middle position of scanning an angle of about 50° with the processed surface, which means that the specimen remains well observable in SEM even during approximately tangential milling by FIB. Unfortunately, during one scanning of the milled surface by the FIB beam there appears the above mentioned curtaining effect on the specimen surface which must be removed by polishing. Heretofore-known methods and commonly used manipulators, however, are not able to ensure the polishing so that the surface can be observed by the SEM beam in both positions, i.e. also in the tilted position, which is necessary for checking the polishing process permanently or at least in selected intervals, without any further manipulation with the specimen. This represents a major disadvantage incompatible with numerous applications, because at least in one position the milling is performed out of the field of view of the SEM, i.e. blindly, which may result even in unwanted milling and destruction of the structures which should have been observed. To tilt the specimen, it might be also necessary to change the specimen holder. In this case, the angle of the specimen tilt is defined by the angle of the tilt of the holder, i.e. it is fixed and it is impossible to change it dynamically, which poses another disadvantage.

Patent application WO 2013039891 for removing curtaining effect recommends that planarization of the examined structure surface is executed. This is achieved through milling in either tangential or nearly tangential direction to the specimen surface before the cut itself is performed. If the curtaining effect appears due to non-homogeneity of the cut itself, which is true in most cases, this solution is functional only to a limited extent.

Patent applications WO 2013082496 and WO 2012103534 specifically focus on preparation of specimens for transmission electron microscopy, hereinafter referred to as TEM. Apart from other things, they also deal with curtaining effect reduction during the specimen preparations and propose a method called backside milling. During this process TEM lamellas get thinner from the silicone substrate side, which is homogeneous and therefore curtaining effect does not originate in it. Curtaining effect appears in the structures underneath the silicone and it is insignificant if the examined layer lies directly below the silicone plate. A method to remove surface defects in the silicone substrate has been also designed.

The method described in these applications is specifically focused on the preparation of ultra-thin TEM lamellas, it concerns shallow cuts only and materials containing homogeneous silicone layer with the curtaining effect reduction occurring only closely underneath the aforementioned layer.

SUMMARY OF THE INVENTION

The aforementioned drawbacks are eliminated by using the presented method of processing the specimen in the apparatus with two or more particle beams and the apparatus designed for the execution of the method. Particle beams go through columns during the specimen processing. The milled side of the specimen is processed by scanning with the first particle beam and observed through scanning by the second particle beam. The axis of the first beam and the axis of the second particle beam are skew or intersecting when impinging on the specimen in the middle scanning position. Specimen is at first milled by scanning by the first particle beam in the first position of the specimen, where the axis of the first particle beam and the surface of the milled side form the angle $\xi$, the value of which ranges from 0° to 30°. After the processing the milled side tilts to the second position around the axis of the specimen tilt. In this second position another milling through re-scanning the same milled side is executed by the first particle beam, which is still oriented to this side so that the axis of this first particle beam again forms the angle the value of which ranges from 0° to 30°, with the plane of the milled side for the whole time of scanning. The essence of the new method is that the axis of the tilt of the specimen intersects the milled side and in the case of all the aforementioned positions and movements of the specimen during and/or after milling with the first particle beam the second particle beam impinges on the milled side, too. The second particle beam scans through the selected area of the milled side so that the axis of the second particle beam forms angles of <90° with the normal to the plane laid through the milled side during the whole time of scanning with the second particle beam. The process of milling by the first particle beam is either checked permanently or at selected intervals by observing through the second particle beam. The observation is done at the same position of the specimen and the same position of the columns of the particle beams apparatuses as the milling.

It is advantageous if the axis of the tilt of the specimen intersecting the milled side is perpendicular to the plane laid through the milled side.

In the middle position of scanning, the axis of the second particle beam may form the angle $\omega$ with the normal to the plane of the milled side of the specimen, this angle being the same for both tilts of the specimen around the axis of the tilt.

There is yet another option, i.e. the tilt around the axis of the tilt of the specimen is continuous and scanning by the first particle beam is executed at the same time as the tilting. If the tilt changes, the milled side of the specimen remains in the field of view of both the first and the second particle beams and the absolute values of the angles of the tilt are arbitrarily adjustable in the interval of <0°, 30°).

It is also advantageous if the specimen tilts around the tilt axis by the angle $\alpha$ before the milled side of the specimen is processed by the first particle beam. Before the milled side of the specimen is processed for the second time by the first particle beam, the specimen tilts around the axis of the tilt by the angle β, the angles α and β being oriented in opposite directions. This step can be modified in the sense that the angles are identical at the absolute value. The absolute value of 10° is advantageous.

During the continuous change of the specimen tilt around the axis of the tilt of the specimen under simultaneous milling, or after the milling in the first position of the specimen followed by the milling in the second position of the specimen, in which the specimen is tilted around the axis of the tilt of the specimen with respect to the first position, the milled side of the specimen gets polished which results in the curtaining effect reduction.

For sake of compensation of the tapering angle caused by processing of the specimen by the first particle beam it is advantageous if that angle ξ at its absolute value is identical to the absolute value of this tapering angle, so that it is guaranteed that the specimen is processed in the required direction of the milled side.

In one advantageous embodiment, the milling by the first particle beam stops in the precisely selected area of the processed specimen, this area being determined by simultaneously observing the image of the milled side of the specimen by the second particle beam.

In order to get an image of the 3D specimen structure or structure located deeper under the specimen surface, the aforementioned process of tilting in two positions around the axis of the tilt of the specimen and milling in each of these positions by the first particle beam while observing by the second particle beam either concurrently or at selected intervals, repeats periodically. It is also possible that milling is repeated periodically while the specimen tilt around the axis of the specimen tilt changes continuously and the second particle beam observes the process either concurrently or at selected intervals. During each repetition of this cycle the axis of the first particle beam shifts by a selected value deeper in the processed specimen either by the first particle beam axis shift and/or by the specimen shift.

There is yet another possibility, with the second particle beam impinging on the milled side of the specimen so that the axis of the second particle beam in the middle position of scanning forms the angle ω ranging from 20° to 50°, typically 35°, with the normal to the plane laid though the milled side.

There is yet another possibility—the first particle beam axis, the second particle beam axis and the axis of the tilt of the specimen are in the same plane.

The first and the second particle beams can be any combination selected from the following groups: electron beam, ion beam, ion beam with metal ions, or ion beam with plasma source. Both the first and the second beam can be focused.

Another improvement consists in the fact that the specimen tilts and/or turns around first other axis and/or second other axis; these axes differing from the axis of the tilt of the specimen and from each other. This variant allows for a modification, i.e. the first other axis, the second other axis and the axis of the tilt of the specimen are mutually intersecting or skew. The first other axis and/or the second other axis can deviate from the axis of the tilt of the specimen by an angle of 90° or near 90°. Another further option is that the first other axis is deviated from the axis of the first particle beam in the middle position of scanning by an angle of 0-30° and/or the axis of the first particle beam and/or the axis of the second particle beam are deviated from the second other axis by an angle of 90° or near 90°.

In one advantageous embodiment, the specimen is moveable in three directions which are perpendicular to each other.

To execute the aforementioned method, the apparatus which contains at least two particle beam sources is used with the particle beams passing through the first and the second columns. The first and the second columns are equipped with electric or electromagnetic scanning device for generating at least two force fields which are approximately perpendicular to each other. The axes of at least two of these columns are intersecting or skew. Lines of force of the force fields of the given column are deviated by an angle of 90° or near 90° from its axis. The apparatus also contains the first set of manipulators represented by at least one manipulator for the specimen attachment, which is tiltable around at least one axis, which is identical to the axis of the tilt of the specimen attached to the first set of manipulators. The essence of the new apparatus consists in the fact that the axis of the tilt of the first set of manipulators intersects the area designed for the processed specimen attached to this first set of manipulators. At the same time, the first set of manipulators is placed in such a way that the area where the specimen is attached to the first set of manipulators is intersected by the axis of the first column and the axis of the second column. Deviation of the axis of the tilt of the first set of manipulators with respect to the axis of the second column is different from 90°, and the deviation of the axis of the tilt of the first set of manipulators with respect to the axis of the first column is in the closed interval from 90° to 60°.

It is advantageous if the tilt around the axis of the tilt of the first set of manipulators is adjustable smoothly at least within the range between +10° and −10°.

Another further possibility is that the apparatus is adapted in such a way that the lines of force of the first force field of the first electromagnetic or electric scanning device deviate from the axis of the tilt of the first set of manipulators by an angle of 90° or near 90°. Deviation between the lines of force of the first field of force of the second electromagnetic or electric scanning device and the axis of the tilt of the first set of manipulators ranges between 40° and 70°, typically it is 55°. There is yet another possible configuration where the axis of the tilt of the first set of manipulators deviates from the axis of the second column by an angle in the range between 20° and 50°, typically it is 35°. At the same time, there can be a deviation between the axis of the first column and the axis of the second column ranging between 40° and 70°, typically it is 55°. Another improvement is represented by the fact that the axis of the tilt of the first set of manipulators intersects the axis of the first column and/or the axis of the second column while the point of intersection of at least two of the three axes is in the area designated for the processed specimen attached to the first set of manipulators.

Any combinations selected from the following groups—electrons, ions, metal ions, or plasma source—can be sources of the first and the second particle beam. The first and the second columns can also be equipped with components for the beam focusing.

In an advantageous embodiment, the first set which consists of at least one first manipulator is attached to the second set which consists of at least one second manipulator. The second set of manipulators advantageously contains components movable in two or three mutually perpendicular directions and components for tilting and/or turning around the third and/or the fourth axis. The third and the fourth axes vary from the axis of the tilt of the first set of manipulators and also from each other. It is advantageous if the third and the fourth axes and the axis of the tilt of the first set of manipulators are mutually intersecting or skew. It is also advantageous if the axis of the tilt of the first set of manipulators deviates with respect to the third axis and/or to the fourth axis by an angle of 90° or close to 90°. In a specific embodiment the axis of the first column deviates by an angle of 0°-30° from the third axis and/or the axis of the first column and/or the axis of the second column deviates from the fourth axis by an angle of 90° or near 90°.

The advantage of the aforementioned method and apparatus consists in enabling milling and polishing of the specimen surface with the first particle beam under various angles of the tilt of the specimen, while the angles can change dynamically during polishing with no shift from the field of view of the first particle beam caused by the change of the angle of the tilt of the specimen. All this is possible either at selected intervals or concurrently with the observing by the second particle beam. To make this observation possible, no further manipulation with the specimen or other parts of the apparatus is necessary. Milling and polishing is permanently controlled in real time and it is possible to stop it exactly in the place of structure which is to be examined. This structure is nearly perfectly smooth due to the polishing. It is also an advantage that the proposed method and apparatus are not limited by material composition of the specimen, they do not require prior planarization of the surface, they also work in cases when the cut through the specimen is non-homogeneous and they are applicable even to deeper cuts at the order of hundreds of μm. These important possibilities are enabled by the presented invention especially due to the addition of the specimen tilt axis intersecting the milled side which is further polished and observed.

BRIEF DESCRIPTION OF THE DRAWINGS

The method of the specimen processing in the apparatus with two of more particle beams and the apparatus for its execution will be further explained using the attached drawings.

Figure 2A:
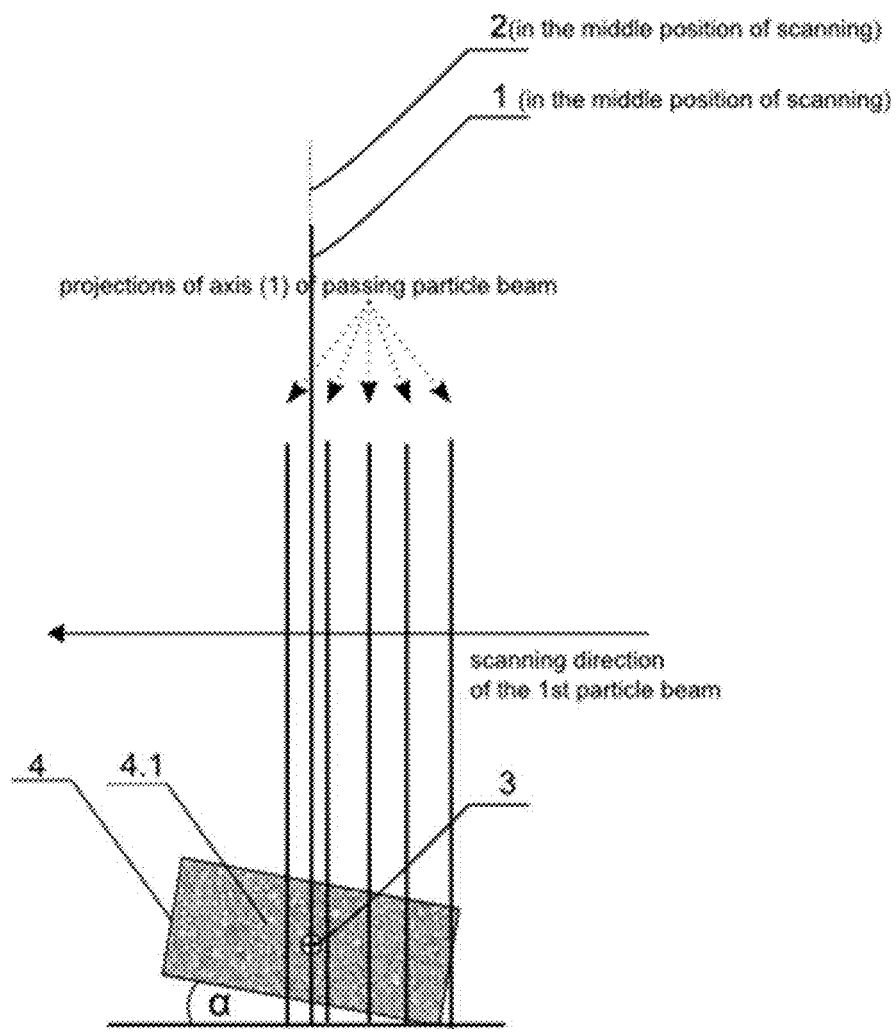
Figure 2B:
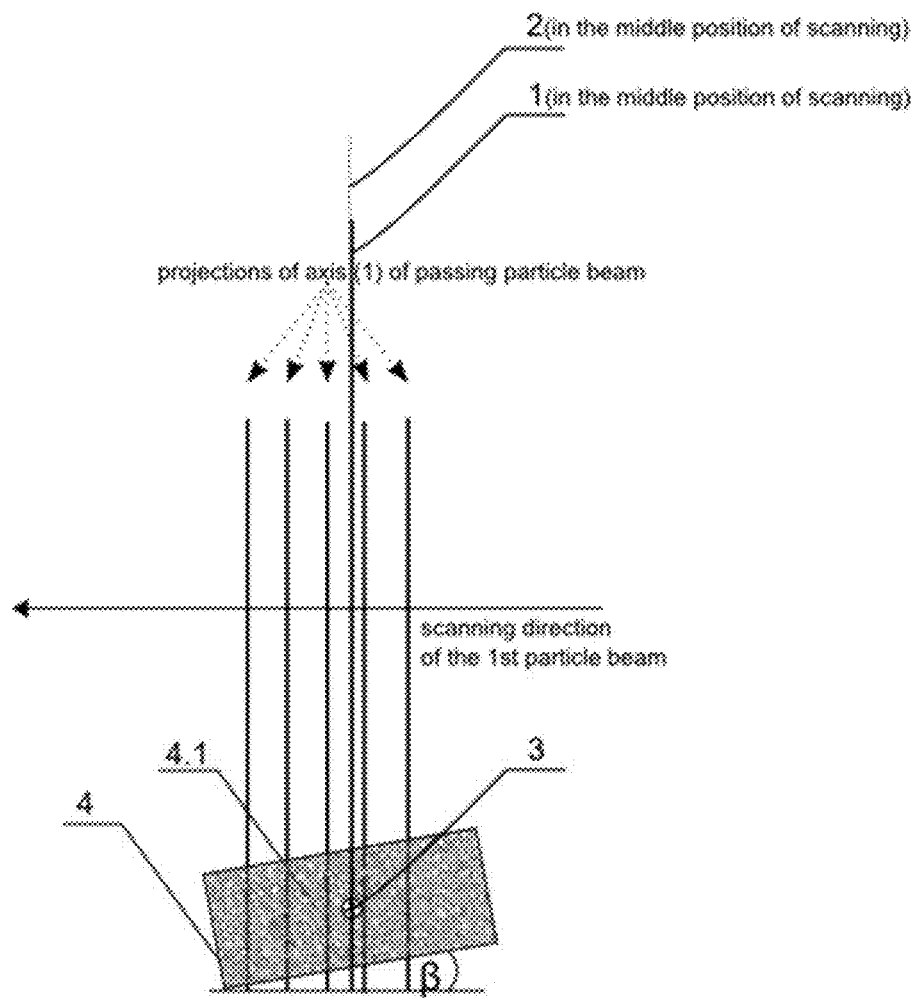

The principle of the curtaining effect removal within the presented invention is schematically illustrated in FIG. 2a and FIG. 2b. The process of scanning by the first particle beam through the milled side of the specimen in the case of two reciprocally tilted positions of the specimen is demonstrated there. The positions of the first and the second particle beam in the middle position of scanning, as well as the axis of the tilt of the specimen are illustrated in these figures.

Figure 3:
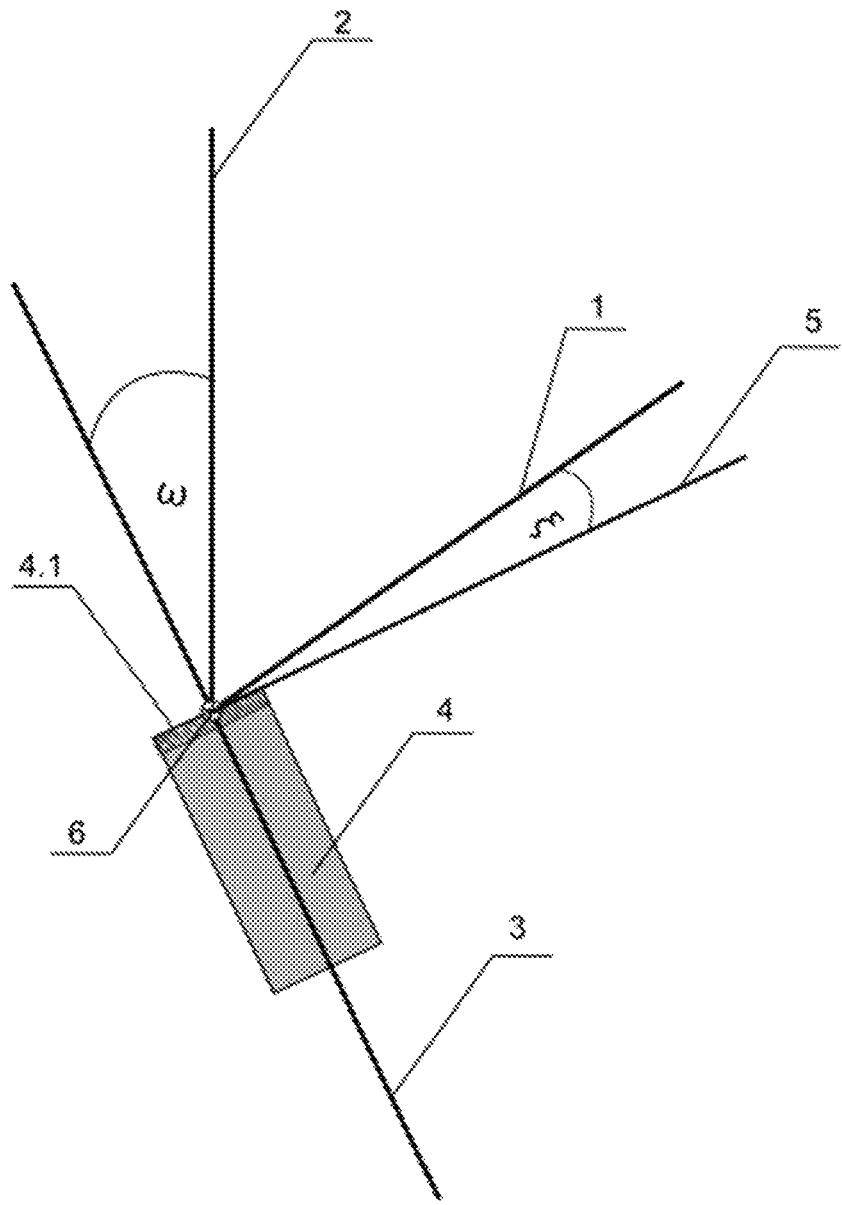

FIG. 3 illustrates another example embodiment with the first and the second other axis of rotation or tilt 5 and 6 and including the tapering angle compensation using the angle ξ.

Figure 4:
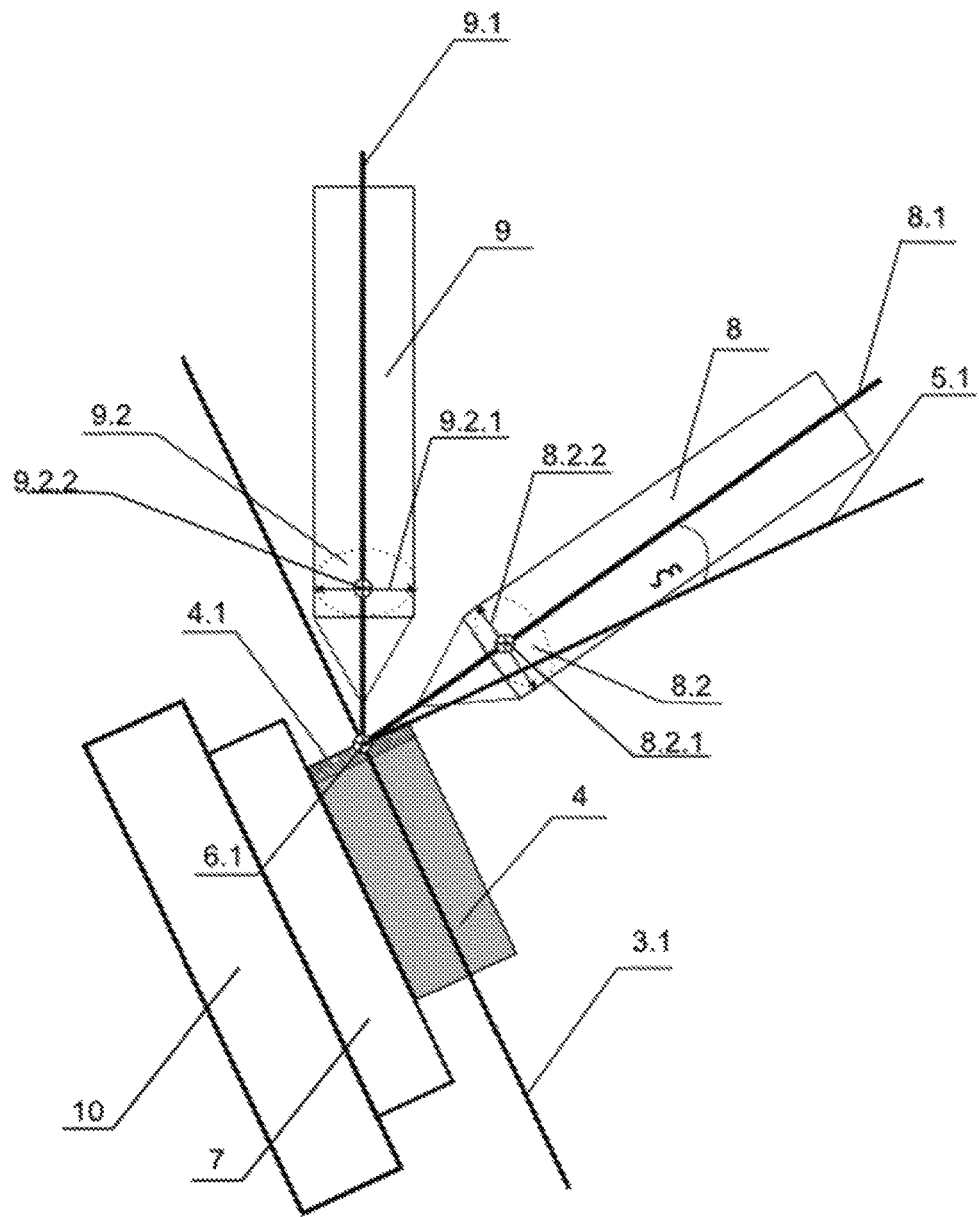

In FIG. 4, an example embodiment of the apparatus for the execution of the presented invention with schematically drawn columns of both devices with particle beams is illustrated, two sets of manipulators and the tilt and/or rotation axes of these manipulators are schematically demonstrated here, while the translation axes are omitted for simplicity reasons. For simplicity reasons, the manipulators are drawn only as blocks, without any detailed demonstration of their construction, which may vary yet the same effect is achieved. The tapering angle compensation using the angle ξ also illustrated in the figure. In the same figure, the directions of resulting lines of force are shown, which deflect the beam in the scanning devices of both columns. This drawing is really only a schematic illustration of the resulting directions in which the beams are scanning; in reality the scanning device may have several levels with more electrical or magnetic fields.

Figure 5A:
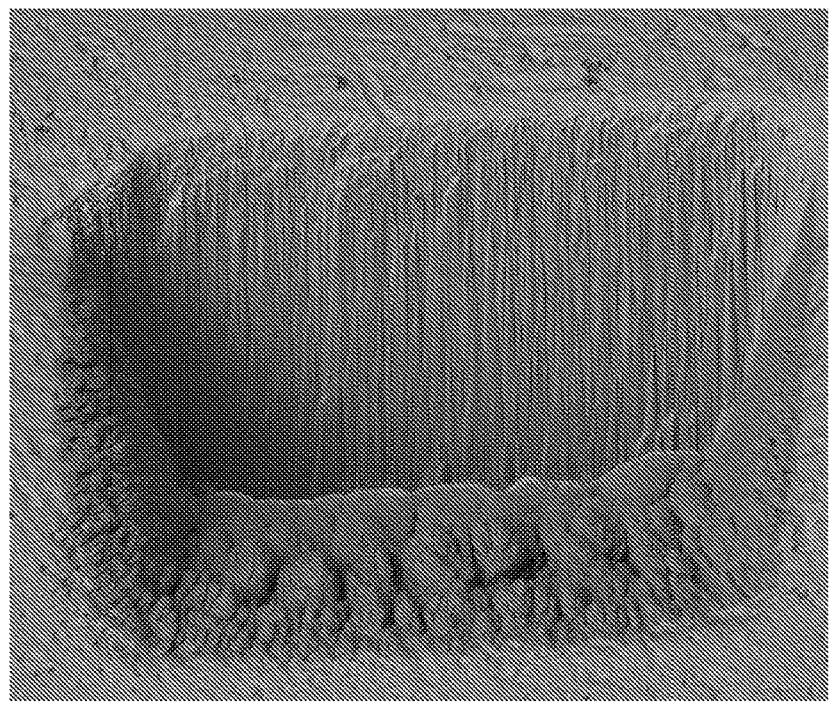
Figure 5B:
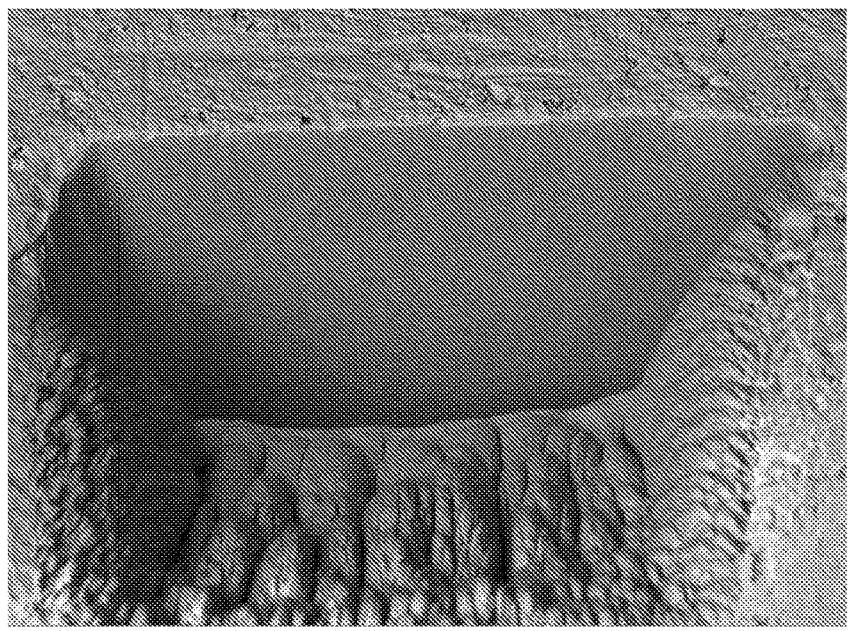

FIG. 5a and FIG. 5b provide illustrations of a milled surface before and after polishing.

EXAMPLES OF PREFERRED EMBODIMENTS

Figure 1:
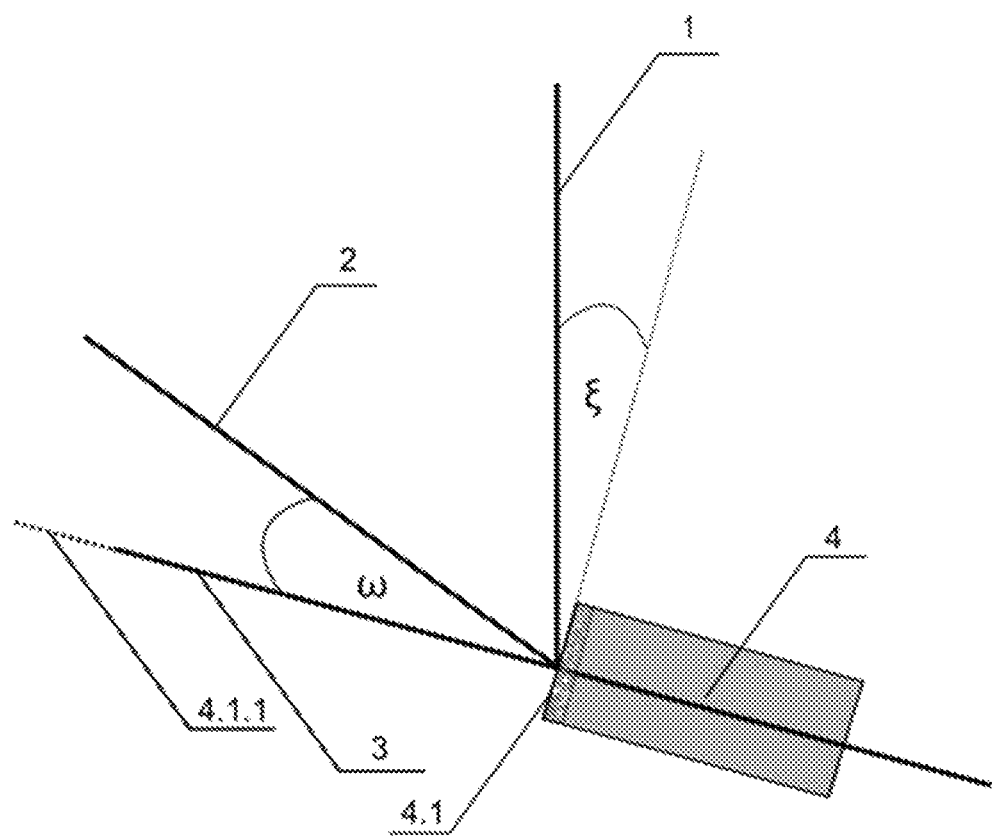
FIG. 1 demonstrates one of the example embodiments of the invention with the highlighted axes of beams, specimen, milled side of the specimen and the axis of the tilt of the specimen in the section passing through the plane of the first and the second particle beam axes.

The method of specimen processing in the apparatus with two or more particle beams may be realized, for example, in the embodiment the complete illustration of which is shown in FIG. 1. For clarity's sake, the figure only illustrates the parts of the apparatus which are important from the point of view of the presented invention principle, i.e. the axes or particle beam columns, manipulator sets, axis of the tilt of the specimen or of the tilt of the manipulators and the examined specimen with processed surface. It is also necessary to bear in mind that with respect to the configuration demonstrated in the figure, a wide range of turning of individual parts of the apparatus, which do not impede with the function principle of the presented invention's method, is possible.

In FIG. 1, an example configuration for the presented invention execution is schematically illustrated. It is the projection into the plane of the axis 1 of the first particle beam in the middle position of scanning and the axis 2 of the second particle beam in the middle position of scanning in the example configuration, where these axes are in the same plane. The condition, under which the plane of axes 1 and 2 shall be common, is not essential for the functioning of the invention. The case shown in FIG. 1 is also special because the axes 1, 2 and the axis 3 of the tilt of the specimen 4 intersect at one point on the milled side 4.1 of the specimen 4, which is not a necessary condition for the functioning of the invention either. It suffices, that the first particle beam, during the scanning, impinged on the milled side 4.1 at an angle of 0°-30° and the second particle beam impacted during the scanning on the milled side 4.1 at an angle other than tangential, while the axis 3 of the tilt of the specimen 4 intersects the milled side 4.1. FIG. 1 also illustrates an example configuration, where the axis 3 of the tilt of the specimen 4 is perpendicular to the plane laid through of the milled side 4.1 of the specimen 4. These special conditions were chosen for greater simplicity of the explanation, while the presented invention is, of course, not limited only to the configuration mentioned in FIG. 1 and series of differently shifted, turned and other configuration variants would function similarly.

In the configuration according to FIG. 1, the first particle beam impinges on the milled side 4.1 of sample 4 it mills this side and its axis 1 in the middle position of scanning, thus for zero deviation of the beam by the scanning device, forms with the milled side 4.1 the angle ξ, the value of which is usually between 0° and 30°. This angle serves for the compensation of the tapering angle of the surface created by processing using the first particle beam so that the milling took place in the plane of the milled side 4.1. The tapering angle commonly results from the machining of the specimen by the focused ion beam. The value of the convergence angle usually depends on the given conditions of processing, for example on the current and spot size of the ion beam and on the material of the specimen. To mill the surface of the specimen in the plane of the milled side 4.1 the specimen 4 must be set into the position, where the milled side 4.1, which is examined by the operator, forms an angle ξ with the axis 1 of the first particle beam, while this angle ξ and the convergence angle are equal for the given conditions of processing at their absolute value. In this example configuration, the first particle beam impinges on the plane of the side 4.1 at an angle ξ, in addition to that it scans in the plane tilted by the angle ξ to the plane of milled side 4.1 so that it passes through the whole surface which is to be processed which leads to the milling in the plane of this milled side 4.1.

Localisation and declination of the milled side 4.1 inside the specimen 4 depends on what structures are inside the specimen and which of these are to be examined. It is convenient, if the side 4.1 is parallel with the plane where the examined structure is located. The position of the specimen 4 shall be set based on the above mentioned, either fixed or using other axes of tilt and/or rotation, as described in the commentary to FIG. 3. At the same time, the specimen 4 must be oriented in such a way that the axis 3 of the tilt always intersects the selected milled side 4.1. This objective can also be reached either by attaching the specimen 4 in a desired position or by properly utilizing other axes of tilt and/or rotation described in the commentary to FIG. 3.

The second particle beam is also directed to the milled side 4.1 of the specimen 4, where the axis 2 of the second particle beam forms the angle ω, which is different from 90°, during the whole time of scanning by this beam, with the normal line 4.1.1 to the plane laid through the milled side 4.1 of the specimen 4, which means that this side can be imaged for the whole period of time using the second particle beam. The second particle beam scans the area, selected by the operator, of the milled side 4.1 of the specimen 4. The imaging is performed in a manner known in apparatuses with particle beams, i. e. due to the interaction of the second particle beam with the surface area of the specimen there occurs an emission of secondary particles or radiation, which can be further detected by relevant detectors, while the signal of these detectors is synchronized with the scanning using the second particle beam.

In one example embodiment, the magnitude of the angle ω is from 20° to 50°, while the typical magnitude is 35°. After the first scanning of the first particle beam, the milling of the surface layer from the milled side 4.1 of the specimen 4 is executed, but due to various material and milling parameters the resulting effect is an uneven surface with grooves in the direction of the beam, the so called curtaining effect appears. With regard to this unevenness of the surface of the milled side 4.1 it is necessary to consider the normal line 4.1.1 as a normal line towards the plane laid through the milled side 4.1. To eliminate the curtaining effect, it is necessary to perform at least one more scanning, leading to further milling by the first particle beam across the specimen surface, which is covered by grooves appearing in connection with the first scanning. This additional scanning of the milled side 4.1 by the first scanning, which will be marked by the same number for clarity's sake, must be done in such a way that the grooves caused by first milling are reduced as much as possible.

The principle of these grooves reduction, and thus the reduction of the curtaining effect, is demonstrated in one example embodiment in FIG. 2a and FIG. 2b. There is the projection into the plane laid though the milled side 4.1 of the specimen 4 during the first milling and the second milling. There are schematically shown projections of axis 1 of the first particle beam deflected by the scanning when this axis runs across the milled side during the first and the second milling. The direction of the scanning illustrated in the figure is only one of numerous possible directions. The grooves are created in the direction of these projections of axes. In FIG. 2a, there is the first step in one example configuration illustrated, where the first milling is executed of the side 4.1 of the specimen 4 in the position when the specimen 4 is tilted by the angle α around the axis 3 of tilt of the specimen 4. In FIG. 2b there is, on the other hand, the second step demonstrated, with the second milling of the same surface of the specimen 4 in the position turned by the angle β, while in this example configuration the angle β is inversely oriented towards the angle α. The grooves created during the first and the second milling form the angle the magnitude of which is α+β, and they cross each other and therefore they eliminate each other to a certain degree. It shall be pointed out that for the invention to function properly, it is only necessary that the grooves created during the first milling are adequately eliminated by the grooves from the second or next milling and vice versa. Therefore it is not necessary for the specimen to be turned during the first milling, it is sufficient to turn it only during the second milling, and also it is not a condition that the angles of turning are inversely oriented; in principle, it is sufficient if the grooves created during the first and second milling forma an adequate angle, usually in the interval of 5°-25°. In an advantageous embodiment, the angle between the grooves, which appeared during the first and second milling, is 20°. Another embodiment which is even more advantageous does not deal with milling in two fixed positions only but rather mills while the specimen 4 is continuously tilting around the axis 3, which results in nearly flawless polishing of the milled side 4.1 of the specimen 4.

The efficiency of this process is well illustrated in FIG. 5a and FIG. 5b. FIG. 5a contains a picture of the surface milled by the first particle beam to see what the surface looks like before polishing. It is evident that the milled side is covered with distinctive grooves. In FIG. 5b, there is the same surface after being polished—one can see that the grooves disappeared and the nice smooth surface emerged instead. Both pictures were made using the second particle beam by means of detection of secondary particles, the emission of which was caused by the particle beam. The polishing and thus the reduction of curtaining effect is, as has already been mentioned, possible due to the tilt around the axis 3 of the tilt of the specimen 4, which—as seen clearly from the FIG. 1—intersects the milled side 4.1 of the specimen 4. Due to this reciprocal position of the axis 3 of the tilt of the specimen 4 and of the milled side 4.1 along with the adjustment of the axis 1 of the first particle beam and of the axis 2 of the second particle beam, which is described above, it is possible to simultaneously or alternately tilt, mill, polish and observe the specimen 4, while even after the tilt around the axis 3 of the tilt of the specimen 4 for the purpose of polishing the milled side 4.1 remains in the field of view of both beams. Tilting around the axis 3 of the tilt of the specimen 4 may be either static so that the specimen 4 is milled in two fixed positions, or dynamic, where the specimen 4 is milled during continuous simultaneous tilting.

The first particle beam or the second particle beam do not have to impinge on the specimen nor do they have to scan permanently. Apart from the simultaneous impingement of the first and second particle beam on the milled side 4.1 of the specimen 4, it is also possible to alternate the simultaneous or individual use of these beams in selected time intervals. This means, among other, that milling by the first particle beam may be observed by the second particle beam either directly in real time, which requires both beams to be simultaneously turned on and not blanked, or in chosen time intervals, while in this second case there is an alternation in the simultaneous and/or individual switching on and/or blanking of both beams. It is possible to apply a method, where the first beam mills the specimen surface, then it is blanked, the observation is performed by the second particle beam, then the first beam is unblanked, after what another milling is executed, the first beam is then blanked again and another observation by the second particle beam is performed. The second particle beam may be turned on/unblanked either permanently or only in time intervals, which follow each milling. When the first particle beam is not scanning over the milled side permanently and the beam is blanked after one phase of milling and/or for example in the moment when a more thorough examination of the created surface by the second particle beam is necessary, the redundant destruction of the milled side by the first particle beam is eliminated.

It is often necessary to study structures, which are deep under the surface of the specimen 4. In this case, there is a shift in the scanning of the first particle beam in the direction of the depth of the specimen 4, which can be achieved either by shifting the axis of the beam by means of a scanning device, or by the shift of the specimen 4 itself. Due to repeating the process of milling, polishing and shifting of the milled area into the depth of the specimen, a 3D image of the examined specimen 4 can be acquired in high quality, because the milled areas do not suffer from the curtaining effect. Due to the fact that the presented invention allows for controlled milling and polishing during the simultaneous observation by the second particle beam or when the observation by the second particle beam is performed at chosen intervals, it is possible to stop the milling timely, when it gets to the point which should be thoroughly examined, which is a common case in the study of TSV structures. The destruction of the structure to be studied is thus eliminated, and it is possible to study in detail the high-quality, polished and grooves free surface of this structure.

In the presented invention, the first and the second particle beams are any combination selected from the group of electron beam, ion beam with metal ions or ion beam with plasma source. The most advantageous is the configuration where the first particle beam, performing the milling, is an ion beam an ion beam with plasma source being suitable for fast milling. The observation is the most advantageous when the second particle beam is an electron beam, as it does not cause destruction of the examined surface when adjusted properly. However, other methods of observation are not excluded. The first and the second beams are advantageously focused; therefore it is possible to focus them on the area of the specimen 4.

The invention, however, is not limited to two beams only, there can be any number of other beams according to the type of necessary analysis, there can be a beam of a different type then the aforementioned ones, for example, a laser beam. It is, of course, convenient if, besides the mentioned tilt of the specimen 4 around the axis 3, it is possible to manipulate the specimen 4 in another way; the best way is without the need to open the apparatus chamber. Therefore it is convenient to shift and/or rotate the specimen inside the chamber so that the milled and/or observed area was selected and moved into the field of view of both particle beams so that the declination of milled side 4.1 could be chosen, and the working distance could be changed, so that different specimens placed in the chamber could be observed, etc. For this purpose, it is convenient to expand the invention by other options of tilt and/or rotation and/or shift of the specimen.

One of the possible configurations of auxiliary axes of the tilt and/or rotation of the specimen 4 is shown in FIG. 3. It is necessary to keep in mind that the axes in the real configuration do not have to intersect in one plane or at one point. To facilitate the performance of the aforementioned invention by the first other axis 5 of the tilt and/or rotation of the specimen 4 and by the second other axis 6 of the tilt and/or rotation of the specimen 4, it is sufficient if they are in relation to each other and also with respect to and to the axis 3 of the specimen 4 intersecting or skew. For the simplicity's sake, FIG. 3 illustrates the situation, where the projections of axes 5, 6, and 3 intersect in one point.

The first other axis 5 is shown, around which it is possible to rotate the specimen 4 or to rotate the stage with several specimens in a way that the desired one reaches the field of view of the particle beams. It is advantageous, if the first other axis 5 forms an angle of approximately 90° with the axis 3 of the tilt of the specimen 4 used for the reduction of curtaining effect. The axis deviation or deviation of any other lines is in the text defined as follows: if they are intersecting lines in a plane, their deviation should be the magnitude of each acute or right angle, which is created by the lines. The deviation of two parallel lines is 0°. The deviation of two skew lines is the deviation of two intersecting lines passing through a chosen point in space in parallel with the given skew lines. In FIG. 3, the second other axis 6 is also illustrated, around which the specimen 4 may be tilted so that the side of the specimen which is designed for milling gets in the position where it forms the angle $\xi$ in the interval of 0°-30° towards the first particle beam. Without these axes 5 and 6 the apparatus may operate, but the operator would be forced to set firmly the direction, in which the specimen 4 would be processed, and thus the position and declination of the milled side 4.1, and it would be impossible for the operator to change this position and declination without interrupting the process.

In one example embodiment, to which however the invention should not be limited, the first other axis 5 and/or the second another axis 6 deviate from the axis 3 of the tilt of the specimen 4 by an angle of 90° or near 90°. It is also advantageous, when the first other axis 5 deviates from the axis 1 of the first particle beam in the middle position of scanning by an angle of 0-30° and/or the axis 1 of the first particle beam and/or the axis 2 of the second particle beam deviate from the second other axis 6 by an angle of 90° or near 90°. Evidently, there can be more axes of tilt and/or rotation than illustrated by FIG. 3.

The invention can be further expanded by the shift of specimen 4, usually in three reciprocally perpendicular directions X, Y, and Z, but shifts in directions forming other angles are also possible if required by the application.

The above mentioned options of other rotations and/or tilts of the specimen around the axes 5 and 6 along with the shift of the specimen, for example, in three reciprocally perpendicular directions allow for greater comfort during the carrying out of the above mentioned invention.

FIG. 4 presents a schematic illustration of one of the possible apparatuses for the presented invention execution. Parts of the apparatus that are not important for the execution of the invention are omitted in the picture. In the picture is shown the projection into the plane of axis 8.1 of the first column 8 of the first apparatus with the particle beam and of axis 9.1 of the second column 9 of the second apparatus with the particle beam in an example configuration, where the axes 8.1 and 9.1 are in one plane. This condition is not vital for the functionality of the invention. The only condition concerning the axes 8.1 and 9.1 is that they have to be mutually intersecting or skew. FIG. 4 also illustrates schematically the first set 7 of manipulators with its axis 3.1 of the tilt. It is demonstrated as a block only, its constructional configuration may vary and it may be conceived as one manipulator or as a set of manipulators allowing more movements than the tilt around the axis 3.1. The axis 3.1 of the of the tilt of the first set 7 of manipulators is identical with the axis 3 of the tilt of the specimen 4 attached to this first set 7 of manipulators, because the first set 7 of manipulators and the specimen 4 attached to the set 7 of manipulators tilt together.

The case which is illustrated in FIG. 4 is also special in the sense that projections of axes 8.1, 9.1 and the axis 3.1 of the tilt of the first set 7 of manipulators intersect in one point on the milled side 4.1 of the specimen 4, which is not a vital condition for the functioning of the invention either, even though for the invention execution this configuration is advantageous. FIG. 4 further shows the example embodiment, where the axis 3.1 of the first set 7 of manipulators is perpendicular to the plane laid through the milled side of the specimen 4. These special conditions were chosen for greater simplicity of the explanation, while the presented invention is not limited only to the configuration illustrated by FIG. 4 and also series of differently shifted, turned and other variants would feature similar functioning.

For the functioning of the invention it is also advantageous when the first set 7 of the manipulators allows for the tilt to around the axis 3.1 of the tilt at least in the interval of +10°, −10° and when this tilt is smoothly adjustable.

Advantageous configuration shown in FIG. 4 serves, apart from other things, to illustrate a selected advantageous configuration of axes; i.e. of the axis 3.1 of tilt, of the axis 8.1 of the first column 8 and of the axis 9.1 of the column 9. However, for the functioning of the invention it is sufficient that the position of these axes meet the further three conditions given below. The first condition is that the axis 8.1 of the first column 8, the axis 9.1 of the second column 9 and the axis 3.1 of the tilt of the first set 7 of manipulators intersect the area, where the specimen 4 is held by the first set 7 of manipulators. Another condition is that the axis 3.1 of the tilt of the first set 7 of manipulators features a deviation different from 90° with respect to the axis 9.1 of the second column 9, which is necessary to ensure that the particle beam passing through the second column impacts on the milled surface in other than tangential direction, enabling the beam to image the surface. The last condition is that the axis 3.1 of the tilt of the first set 7 of manipulators deviates from the axis 8.1 by an angle in the closed interval from 90° to 60°, which is necessary for milling of the selected milled side 4.1. Application of the aforementioned conditions together with a suitable configuration of scanning devices in both columns ensure that the milling and observation of the milled area is performed in such configuration that even when performing a tilt around the axis 3.1 of the tilt of the first set 7 of manipulators, which is necessary for the polishing of the milled surface, the milled surface always remains in the field of view of both beams.

Apart from the axes 8.1 and 9.1 of the columns, FIG. 4 also illustrates the columns of apparatuses with particle beams, i.e. the first column 8 and the second column 9. It is again only a schematic demonstration, the geometric parameters of both columns 8 and 9 may differ, their widths, lengths or the shape of their pole pieces do not have to be the same, etc. In the columns the corresponding scanning devices are schematically drawn together with the resulting directions of the beam deviation. The first column 8 is equipped with the first electric or electromagnetic scanning device 82 for generating of at least two force, i.e. electric or electromagnetic, fields 8.2.1, 8.2.2, the purpose of which is to deviate the beam in the process of scanning. It is convenient if the lines of force of these force fields 8.2.1 and 8.2.2 are perpendicular to one another or form an angle between 70° and 90°. The first scanning device 8.2 may consist of more stages of force fields, or there may be more than two force fields, which combine with one another, in one stage. In this case it is necessary to perceive the fields 8.2.1 and 8.2.2 as resulting directions, in which the beam is deviated. The second column 9 is equipped with the second electric or electromagnetic scanning device 9.2 for generating at least two force, i.e. electric or electromagnetic, fields 9.2.1, 9.2.2, the purpose of which is to deviate the beam in the process of scanning. It is convenient, when the lines of force of these fields 9.2.1 and 9.2.2 are perpendicular to one another or deviate with the value of the deviation between 70° and 90°. The second scanning device 92 may consist of several stages of force fields, or there may be more than two force fields, which combine with one another, in one stage. In this case it is necessary to perceive the fields 9.2.1 and 9.2.2 as resulting directions, in which the beam is deviated. The lines of force of fields 8.2.1 and 8.2.2 deviate by an angle lying in the interval from 70° to 90° from the axis 8.1 of the first column 8, advantageously 90°, and similarly the lines of force of fields 9.2.1 and 9.2.2 deviate by an angle lying in the interval from 70° to 90° from the axis 9.1 of the second column 9, advantageously 90°. An advantageous embodiment with the deviation of 90° is shown in FIG. 4.

It is further advantageous when the lines of force of the first force field 8.2.1 of the first electromagnetic or electric scanning device 8.2 deviate from the axis 3 of the tilt of the first set 7 of manipulators by an angle of 90° or in the interval from 70° to 90°. Due to this fact, the scanning connected to milling is performed in the same or nearly the same plane as the tilting of the milled surface around the axis 3.1 of the tilt of the first set 7 of manipulators. Scanning by the second force field 8.2.2 then serves to deviate the axis of the first particle beam in the direction towards the inside of the specimen 4, along the axis 3.1 of the tilt of the first set 7 of manipulators. Thanks to this, it is possible to examine the structures placed deeper under the surface. Similar effect, i.e. the shift of milling into the depth of the specimen, can also be achieved if the specimen 4 itself is shifted with respect to the column 8. The shift is possible by virtue of the auxiliary second set 10 of manipulators, which is described hereinafter. A combination of both methods is possible, i.e. the shift of the first particle beam and the shift of the specimen in the directions opposite to each other.

It is also advantageous when the lines of force of the first force field 9.2.1 of the second electromagnetic or electric scanning device 9.2 deviate from the axis 3.1 of the tilt of the first set 7 of manipulators by an angle lying in the interval from 40° to 70°, typically 55°.

Geometric parameters of the columns with particle beams usually lead to a convenient configuration, where the axis 3.1 of the tilt of the first set 7 of manipulators deviates from the axis 9.1 of the second column 9 by an angle lying in the interval from 20° to 50°, typically 35°. This position of the axis 3.1 of the tilt may be either fixed, or the axis 3.1 can be tilted into this position using the second set 10 of manipulators consisting of at least one manipulator, which is described in detail hereinafter. This position is advantageous with respect to the common configuration of columns, which is usually as follows: the axis 8.1 of the first column 8 deviates from the axis 9.1 of the second column 9 by an angle lying in the interval from 40°-70°, typically 55°. In this position it is possible to mill with ease the surface which forms an angle in the interval from 0°-30° with the axis 8.1 of the first column 8 and, at the same time even when tilting around the axis 3.1 of the tilt of the first set 7 of manipulators, to observe this surface by the particle beam passing through the column 9.

FIG. 4 also illustrates an extended version of the invention with the auxiliary second set 10 of manipulators schematically shown as a block without further detailed demonstration of a specific construction configuration, which may vary. The auxiliary second set 10 of manipulators consists of at least one manipulator, however, it usually contains more manipulators. The auxiliary second set 10 of manipulators is not vital for the functioning of the presented invention, its addition, however, allows for greater comfort when manipulating with the specimen. For this particular purpose, the first set 7 of manipulators is attached to the second set 10 of manipulators, i. e. the movements of this second set 10 of manipulators also lead to the movement of the first set 7 of manipulators, to which the specimen 4 is attached, and therefore it leads to the movement of the specimen 4. Thanks to the addition of the second set 10 of manipulators it is thus possible to change the working distance, choose between different specimens 4 which may be simultaneously attached to the first set 7 of manipulators, choose the area of the specimen 4 designated for milling and observation, shift the milling further into the specimen 4 depth, choose the declination of the milled surface, etc., and all this without the need to open the apparatus chamber and without the need to manually manipulate with the specimen 4. For this purpose, the second set 10 of manipulators contains components movable in two or three directions perpendicular to one another and/or components for the tilt and/or rotation around the third axis 5.1 and/or around the fourth axis 6.1, where this third axis 5.1 and the fourth axis 6.1 are different from the axis 3.1 of the tilt of the first set 7 of manipulators and also from one another and where they are advantageously intersecting or skew with respect to each other and to the axis 3.1 of the tilt of the first set 7 of manipulators. The third axis 5.1, which serves as the axis of rotation, usually allows for the unlimited range of turning between 0° and 360°. In the case of the fourth axis 6.1, which serves as an axis of tilt, the range of the tilt is limited for a certain interval of angles due to constructional reasons.

In advantageous embodiments, the axis 3.1 of the tilt of the first set 7 of manipulators deviates from the third axis 5.1 and/or from the fourth axis 6.1 by an angle of 90° or the deviation lies in the interval from 70° to 90°. In advantageous configurations, the axis 8.1 of the first column 8 deviates from the third axis 5.1 by an angle of 0-30° and/or the axis 9.1 of the second column 9 deviates from the fourth axis 6.1 by an angle of 90° or lying the interval from 70° to 90°.

For the sake of simplicity, FIG. 4 shows the advantageous situation, where the projections of axes 5.1, 6.1 and 3.1 intersect in one point, which, in this special configuration, is identical with the projection of the point of intersections of the axis 8.1 of the first column 8 and the axis 9.1 of the second column 9. It is necessary to keep in mind that in a real configuration the axes 5.1, 6.1 and 3.1 do not have to intersect in one plane or in one point. To facilitate the carrying out of the aforementioned invention by means of the third axis 5.1 and of the fourth axis 6.1, it is sufficient if the axes 5.1, 6.1 are intersecting or skew to one another as well as with respect to the axis 3.1 of the tilt the first set 7 of manipulators.

Sources of the first and the second particle beam are any combinations selected from the group of sources: electrons, ions, metal ions, or plasma source. At the same time, it is convenient, if the source of the first column 8 is an ion one and the ion plasma source for faster milling, and if the source in the second column 9 is the electron one to avoid the surface destruction during the observation.

The first column 8 and the second column 9 are equipped with components for beam focusing, usually with electromagnetic or electrostatic lenses. The image provided by the second particle beam uses the method which is applied in apparatuses with particle beams, which means that in consequence to the interaction of the second particle beam with the surface area of the specimen there is an emission of secondary particles or radiation, which can be further detected by relevant detectors, while the signal of these detectors is synchronized with scanning by the second particle beam.

The apparatus based on the presented invention may, of course, also contain series of other components, additional columns with beams, detectors, measuring apparatuses and many others, which are not explicitly described herein.

INDUSTRIAL APPLICABILITY

The presented method and apparatus are utilizable for milling and polishing of structures and for observation of these polished structures using apparatuses with particle beams. Thanks to this invention, it is possible to tilt the specimen in a way that a smooth, curtaining effect free surface of the specimen during the milling by one particle beam can be achieved. At the same time the specimen remains in the field of view of the first and the second particle beams. Due to the use of the second particle beam, it is possible to permanently or in selected intervals monitor and/or observe the milled surface without the need of further manipulation with the specimen and/or particle beam columns. Due to this possibility to observe the process of milling in the real time, there is no danger of destructing the observed structure, the process is fast and without inaccuracies which would otherwise be caused by the necessity of further manipulation with the specimen. This method and apparatus can be applied easily in all areas, where there is a need to examine a really smooth surface of the specimen without the artefacts of the curtaining effect type, while also enabling the real time control of the milling process. The presented invention may be, among other, used for the TSV structures and other semiconductor specimens examination, for the examination of polycrystalline specimens, to acquire the 3D image of the specimen structure, etc.

The invention claimed is:

1. Method of processing a specimen in an apparatus with two or more particle beams passing through columns, comprising the steps of:
   a) processing a milled side of a specimen by scanning the specimen with the first particle beam, the processing step comprising the steps of:
   i) milling the specimen a first time by scanning the specimen with the first particle beam in a first position of the specimen, in which an axis of the first particle beam forms an angle with a plane of the milled side for a whole duration of scanning, while the angle has a magnitude in an interval from 0° to 30°, and after milling the specimen the first time, ii) tilting the milled side into a second position around an axis of tilt of the specimen and in the second position, wherein the axis of tilt of the specimen intersects the milled side, and iii) milling the specimen a second time by re-scanning the same milled side again with the first particle beam, which is still directed to this milled side in a way that the axis of the first particle beam forms an angle with the milled side for the whole duration of the scanning, and wherein the angle has a magnitude in an interval from 0° to 30°, and b) observing the milled side of the specimen by scanning the specimen with a second particle beam, wherein the axis of the first particle beam in a middle scanning position and an axis of the second particle beam in a middle scanning position are skew or intersecting when impinging on the specimen in, and wherein during at least part of the processing step, the milled side is impinged by the second particle beam, which scans over a selected area of the milled side in a way that the axis of the second particle beam for the whole time of the scanning by the second particle beam forms an angle less than 90° with a line normal to a plane through the milled side, and wherein, as a consequence, the processing step is either continuously or in selected intervals controlled by the observing step using the second particle beam, while the observing step is performed with the second particle beam at the same position of the specimen and the same position of the first particle beam of the processing step.

2. Method according to claim 1, wherein the axis of tilt of the specimen intersecting the milled side of the specimen is perpendicular to the plane through the milled side.

3. Method according to claim 1, wherein the axis of the second particle beam in the middle scanning position forms an angle which is normal to the plane of the milled side of the specimen, the angle being the same for both tilts of the specimen around the axis of tilt of the specimen.

4. Method according to claim 1, wherein the tilt around the axis of tilt of the specimen is executed continuously during concurrent scanning with the first particle beam, while during change of tilt, the milled side of the specimen remains in a field of view of the first particle beam and of the second particle beam and absolute values of angles of tilt are arbitrarily adjustable in the interval from 0° to 30°.

5. Method according to claim 1, wherein before the first milling step i), the specimen tilts around the axis of tilt of the specimen by a first angle and before the second milling step iii), the specimen tilts around the axis of tilt of the specimen by a second angle, while these angles are inversely oriented.

6. Method according to claim 5, wherein the first and second angles are identical at an absolute value.

7. Method according to claim 6, wherein the absolute value of the first and second angles is 10°.

8. Method according to claim 1, wherein during continuous change of tilt of the specimen around the axis of tilt of the specimen under concurrent milling, or after milling in the first position of the specimen which is followed by milling in the second position of the specimen, which is tilted with respect to the first position of the specimen around the axis of tilt of the specimen, the milled side of the specimen is polished and curtaining effect is thus reduced.

9. Method according to claim 1, wherein to compensate for impact of tapering angle created by processing of the specimen by the first particle beam, the angle is at its absolute value identical to the absolute value of the tapering angle, which guarantees specimen processing in a required direction of the milled side.

10. Method according to claim 1, wherein depending on an image of the milled side of the specimen observed by the second particle beam, the milling by the first particle beam stops in an exactly selected area of specimen being processed.

11. Method according to claim 1, wherein, if it is necessary to get an idea of a 3D structure of the specimen or about a structure located deeper under a surface of the specimen, the method of tilting to two positions around the axis of the tilt of specimen and milling in each of these positions with the first particle beam while the second particle beam is used for observation either concurrently or at selected intervals, periodically repeats, or the milling steps i) and iii) periodically while the tilt of the specimen changes continuously around the axis of the tilt of the specimen and the observing by the second particle beam is done either concurrently or at selected intervals, and during each repetition of this cycle the axis of the first particle beam shifts by a selected value deeper in the specimen being processed either by moving the axis and/or by moving the specimen.

12. Method according to claim 1, wherein the second particle beam impinges on the milled side of the specimen so that the axis of the second particle beam in the middle scanning position forms an angle ranging from 20° to 50°, with the line normal to the plane through the milled side.

13. Method according to claim 1, wherein the axis of the first particle beam, the axis of the second particle beam and the axis of the tilt of specimen lie in the same plane.

14. Method according to claim 1, wherein the first and the second particle beams are any combination selected from the following group: electron beam, ion beam, ion beam with metal ions, or ion beam with a plasma source.

15. Method according to claim 1, wherein both the first and the second particle beams are focused.

16. Method according to claim 1, wherein the specimen tilts and/or turns also around a first other axis and/or around a second other axis, while these axes are different from the axis of the of the specimen and also different from each other.

17. Method according to claim 16, wherein the first other axis, the second other axis and the axis of tilt of the specimen are mutually intersecting or skew.

18. Method according to claim 16, wherein the first other axis and/or the second other axis deviate from the axis of tilt of the specimen by an angle of 90° or near 90°.

19. Method according to claim 16, wherein the first other axis deviates from the axis of the first particle beam in the middle scanning position by an angle from 0° to 30° and/or the axis of the first particle beam and/or the axis of the second particle beam deviate from the second other axis by an angle of 90° or near 90°.

20. Method according to claim 1, wherein the specimen is movable in three directions perpendicular to one another.

* * * * *